United States Patent

Kneuper et al.

Patent Number: 5,679,868
Date of Patent: Oct. 21, 1997

[54] PREPARATION OF GLUTARIC DIALDEHYDE

[75] Inventors: Heinz-Josef Kneuper, Mannheim; Rainer Becker, Bad Dürkheim; Eugen Gehrer, Ludwigshafen; Juergen Schossig, Fussgönheim; Andreas Henne, Neustadt, all of Germany

[73] Assignee: BASF Aktiengesellschaft, Ludwigshafen, Germany

[21] Appl. No.: 571,092

[22] Filed: Dec. 12, 1995

[30] Foreign Application Priority Data

Dec. 15, 1994 [DE] Germany .................. 44 44 709.4

[51] Int. Cl.$^6$ .................................................. C07C 47/12
[52] U.S. Cl. ............................................................. 568/483
[58] Field of Search .................................................. 568/483

[56] References Cited

U.S. PATENT DOCUMENTS

| | | |
|---|---|---|
| 2,546,018 | 3/1951 | Smith et al. . |
| 3,308,069 | 3/1967 | Wadinger et al. ............. 252/455 |
| 4,224,876 | 9/1980 | Warner et al. . |
| 4,448,977 | 5/1984 | Warner et al. . |

FOREIGN PATENT DOCUMENTS

| | | |
|---|---|---|
| 66224 | 12/1982 | European Pat. Off. . |
| 7226488 | 4/1967 | Japan . |

*Primary Examiner*—Bernard Dentz
*Assistant Examiner*—Sreeni Padmanabhan
*Attorney, Agent, or Firm*—John H. Shurtleff

[57] ABSTRACT

A process for the preparation of glutaric dialdehyde by the reaction of alkoxy dihydropyrans of the general formula I

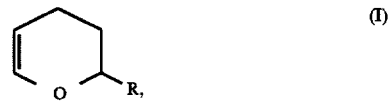

in which R stands for $C_1$ to $C_{20}$ alkoxy, with water at temperatures ranging from 0° to 150° C. and pressures of from 0.01 to 50 bar in the presence of a which microporous, crystalline aluminum silicate catalyst, e.g. a beta-type zeolite or pentasil catalyst having a pore diameter greater than 5.4 Å.

8 Claims, No Drawings

PREPARATION OF GLUTARIC DIALDEHYDE

The present invention relates to a process for the preparation of glutaric dialdehyde by reaction of alkoxy dihydropyrans with water in the presence of microporous, crystalline aluminum silicates having large pores and acting as catalysts.

U.S. Pat. No. 2,546,018 discloses the thermal hydrolysis of alkoxy dihydropyrans at temperatures of from 100° to 200° C. to form glutaric dialdehyde. Acid catalysts are proposed for lowering the reaction temperature.

JP 7,226,488 describes homogeneous acid catalysis using, e.g., $H_3PO_4$. The use of these homogeneous acids as catalysts for the hydrolysis of the alkoxy pyran to glutaric dialdehyde has the drawback that they remain in the system on completion of the reaction and must therefore be neutralized. In this form they cause discoloration of the glutaric dialdehyde or they catalyze polymerization of the glutaric dialdehyde and thus cause undesirable turbidity due to precipitation of the polymer. The polymerization proneness of glutaric dialdehyde is known and is generally substantially suppressed by using it in dilute aqueous solution. Due to these problems different processes have been described, inter alia the use of acid ion exchangers as hydrolysis catalyst (EP-A 66,224, U.S. Pat. No. 4,244,876 and U.S. Pat. No. 4,448,977). These references describe the reaction of alkoxy dihydropyran with water or alcohol to produce hydroxyalkoxy tetrahydropyran or dialkoxy tetrahydropyran as a stable glutaric dialdehyde precursor. Conversion to the desired glutaric dialdehyde must still be carried out subsequently. In addition to this drawback, the inadequate catalyst activity and the short on-stream times achieved by the ion exchangers are unsatisfactory.

It is thus an object of the present invention to overcome the above drawbacks.

Accordingly, we have found a novel and improved process for the preparation of glutaric dialdehyde by the reaction of alkoxy dihydropyrans of the general formula I

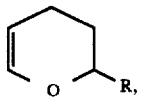
(I)

in which R stands for $C_1$ to $C_{20}$ alkoxy, with water at temperatures ranging from 0° to 150° C. and pressures of from 0.01 to 50 bar in the presence of a catalyst, wherein the catalyst used is a microporous, crystalline aluminum silicate having a pore diameter greater than 5.4 Å.

The process of the invention can be carried out as follows:

The alkoxy dihydropyran I and water may be caused to react at temperatures of from 0° to 150° C., preferably from 30° to 100° C. and more preferably from 40° to 80° C. and pressures of from 0.01 to 50 bar, preferably from 0.1 to 5 bar and more preferably at atmospheric pressure (standard pressure) in the presence of a halogen catalyst to form glutaric dialdehyde.

Suitable hydrolysis catalysts are microporous, crystalline aluminum silicates having pore diameter larger than 5.4 Å, ie from 5.5 to 20 Å, preferably from 5.8 to 15 Å and more preferably from 6 to 12 Å, particularly beta-type zeolites (BEA), and also pentasil (ZSM-5, ZBM-10).

β-zeolites were described for the first time in U.S. Pat. No. 3,308,069. They can be crystallized at temperatures in a range extending from 100° to 150° C. by means of tetraethylammonium hydroxide (TEAOH) having the composition TEAOH: $SiO_2$: $Al_2O_3$: $Na_2O$: $H_2O$, where the $SiO_2/Al_2O_3$ ratio is in a range extending from 10:1 to 200:1, the ratio of $Na_2O$ to TEAOH being from 0:1 to 1.0:1, that of TEAOH to $SiO_2$ being from 0.1:1 to 1.0:1 and that of $H_2O$ to TEAOH being from 20:1 to 75:1. They possess a large-pore, three-dimensional pore system containing 12-membered rings having diameters of 6.5×5.6 Å and 7.5×5.7 Å. The constraint index (method of determination used in U.S. Pat. No. 4,016,218) is between 0.6 and 2.0. Their catalytic action in the preparation of glutaric dialdehyde has been unknown hitherto.

The molar ratio of water to the alkoxy dihydropyran I is usually from 0.5:1 to 100:1, preferably from 1:1 to 20:1 and more preferably from 1:1 to 10:1.

The substituent R in the alkoxy dihydropyran compound is defined as $C_1$ to $C_{20}$ alkoxy, preferably $C_1$ to $C_8$ alkoxy and more preferably $C_1$ to $C_4$ alkoxy such as methoxy, ethoxy, n-propoxy, isopropoxy, n-butoxy, isobutoxy, sec-butoxy, or tert-butoxy, particularly methoxy or ethoxy.

Suitable alkoxy dihydropyrans are preferably 2-alkoxy-3,4-dihydropyrans such as 2-methoxy-3,4-dihydropyran, 2-ethoxy-3,4-dihydropyran, 2-n-propoxy-3,4-dihydropyran, 2-isopropoxy-3,4-dihydropyran, 2-n-butoxy-3,4-dihydropyran, 2-isobutoxy-3,4-dihydropyran, 2-sec-butoxy-3,4-dihydropyran, and 2-tert-butoxy-3,4-dihydropyran and more preferably 2-methoxy-3,4-dihydropyran and 2-ethoxy-ethoxy-3,4-dihydropyran.

Following the saponification reaction, the resulting crude product can be freed from the methanol formed, for example by distillation, so as to give methanol-free glutaric dialdehyde.

Glutaric dialdehyde is used, e.g., in the tanning industry or as a microbiocide.

EXAMPLES

Batchwise Method

Example 1

In a stirred 3-necked flask there are mixed 114 g of methoxy dihydropyran (1 mol) with 57 g of water (3.2 mol) and 5 g of catalyst β-zeolite sold by Uetikon (composition: $SiO_2$ 91%, $Al_2O_3$ 7.8%, $Na_2O$ 0.5%, $K_2O$ 0.7%, surface area (BET) 700 $m^2/g$, pore size in Å 7.6×6.7, 5.5×5.5, particle size 0.2 to 0.5 mm) at 50° C. The degree of conversion is approximately 70% after 90 min and more than 99% after 5 h (as monitored by gas chromatography). After 5 h the mixture is cooled and separated from the catalyst by filtration, and the crude mixture contains 57% of glutaric dialdehyde (as determined by titrimetry).

Example 2

Preparation of the catalyst: 100 g of β-zeolite are exchanged with 1.5 l a 10% ig iron nitrate solution for 2 h at 80° C. It is then washed with water, filtered off, and dried at 100° C. In a stirred 3-necked flask there are mixed 114 g of methoxy dihydropyran (1 mol) with 57 g of water (3.2 mol) and 5 g of the catalyst thus prepared, at 50° C. The degree of conversion is approximately 92% after 90 min and more than 99% after 3 h (as monitored by gas chromatography). After 3 h the mixture is cooled and the catalyst filtered off, the crude mixture containing 58% of glutaric dialdehyde (as determined by titrimetry).

Continuous Procedure

Example 3

Preparation of the catalyst: 220 g of β-zeolite of Example 1 are compacted with 5% of Walocel and 230 g of water for 45 minutes in a kneader. The resulting material is then shaped under a molding pressure of 70 bar to form 2 mm extrudates. These are dried at 110° C. and calcined for 16 h at 500° C. 195 g of these extrudates are exchanged with 3 l of 20% strength NH$_4$Cl solution at 80° C. for 2 h and subsequently washed with 10 l of water. There is then carried out a second exchange with again 3 l of 20% strength NH$_4$Cl solution at 80° C. and the product is washed until free of Cl. Following drying at 110° C. calcination is carried out for 5 h at 500° C.

In a tubular reactor packed with 0.5 l of catalyst extrudates methoxy dihydropyran is hydrolyzed to glutaric dialdehyde by the continuous feed of 35 ml/h of methoxy dihydropyran (0.3 mol) and 15 ml/h of water (0.83 mol) at 60° C. and recycling of 12 l/h of reaction solution. The effluent is monophase and clear. The effluent contains between 23.2 and 24.1% of water (determined by Karl-Fischer tritration), between 54.9 and 56.8% of glutaric dialdehyde (titrimetric determination via the CO number), between 0.6 and 2.2% of methoxy dihydropyran and from 14 to 20% of methanol, and also various acetals (as determined by gas chromatography).

We claim:

1. A process for the preparation of glutaric dialdehyde which comprises reacting an alkoxy dihydropyran of the general formula I

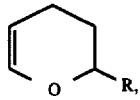

(I)

in which R stands for $C_1$ to $C_{20}$ alkoxy, with water at temperatures ranging from 0° to 150° C. and pressures of from 0.01 to 50 bar in the presence of a β-zealite, catalyst which is a microporous, crystalline aluminum silicate having a pore diameter greater than 5.4 Å.

2. A process for the preparation of glutaric dialdehyde as defined in claim 1, wherein the catalyst used is a pentasil zeolite.

3. A process for the preparation of glutaric dialdehyde as defined in claim 1, wherein R stands for $C_1$ to $C_8$ alkoxy.

4. A process for the preparation of glutaric dialdehyde as defined in claim 1, wherein R stands for $C_1$ to $C_4$ alkoxy.

5. A process for the preparation of glutaric dialdehyde as defined in claim 1, wherein R stands for methoxy or ethoxy.

6. A process for the preparation of glutaric dialdehyde as defined in claim 1, wherein the reaction is carried out at temperatures ranging from 20° to 120° C.

7. A process for the preparation of glutaric dialdehyde as defined in claim 1, wherein the reaction is carried out at pressures-ranging from 0.1 to 10 bar.

8. A process for the preparation of glutaric dialdehyde as defined in claim 1, wherein the reaction is carried out under atmospheric pressure.

* * * * *

UNITED STATES PATENT AND TRADEMARK OFFICE
CERTIFICATE OF CORRECTION

PATENT NO. : 5,679,868
DATED : October 21, 1997
INVENTOR(S) : Heinz-Josef Kneuper, Rainer Becker, Eugen Gehrer, Juergen Schossig and Andreas Henne It is certified that error appears in the above-indentified patent and that said Letters Patent is hereby corrected as shown below:

Item [57]
IN THE ABSTRACT:

In Line 5 (disregarding the formula 1):

after "presence of a", insert --catalyst--;

after "which", insert --is a--.

Signed and Sealed this

Sixteenth Day of June, 1998

Attest:

BRUCE LEHMAN

Attesting Officer

Commissioner of Patents and Trademarks